US007595726B2

(12) United States Patent
Nissels et al.

(10) Patent No.: US 7,595,726 B2
(45) Date of Patent: Sep. 29, 2009

(54) DEVICE WITH DISPLAY AND CONTROL

(75) Inventors: Robert Nissels, Ins (CH); Kurt Friedli, Lyssach (CH); Reto Sigrist, Golaten (CH); Stefan Lindegger, Lotzwill (CH); Philip Etter, Ittigen (CH)

(73) Assignee: Disetronic Licensing AG, Burgdorf (CH)

( * ) Notice: Subject to any disclaimer, the term of this patent is extended or adjusted under 35 U.S.C. 154(b) by 237 days.

(21) Appl. No.: 11/531,659

(22) Filed: Sep. 13, 2006

(65) Prior Publication Data

US 2008/0180268 A1 Jul. 31, 2008

Related U.S. Application Data

(63) Continuation of application No. PCT/EP2005/002696, filed on Mar. 14, 2005.

(30) Foreign Application Priority Data

Mar. 18, 2004 (DE) .................. 10 2004 013 415

(51) Int. Cl.
G08B 1/08 (2006.01)
(52) U.S. Cl. .............................. 340/539.29; 340/686.1; 340/693.5; 345/169; 341/22; 379/433.06
(58) Field of Classification Search .................. 340/540, 340/686.1, 539.29, 539.12, 693.5; 345/700, 345/169, 762; 379/433, 433.06; 455/575.1; 341/22
See application file for complete search history.

(56) References Cited

U.S. PATENT DOCUMENTS

| 5,398,023 | A | 3/1995 | Murray |
| 5,551,850 | A | 9/1996 | Williamson et al. |
| 6,373,501 | B1 * | 4/2002 | Fiero ........................... 715/700 |
| 6,593,914 | B1 * | 7/2003 | Nuovo et al. ................. 345/169 |
| 7,379,762 | B2 * | 5/2008 | Too et al. .................. 455/575.1 |
| 2003/0233071 | A1 | 12/2003 | Gillespie, Jr. et al. |
| 2004/0046791 | A1 * | 3/2004 | Davis et al. ................. 345/762 |
| 2005/0041531 | A1 * | 2/2005 | Sekura ........................ 368/10 |
| 2005/0237704 | A1 * | 10/2005 | Ceresoli ...................... 361/683 |

FOREIGN PATENT DOCUMENTS

| DE | 41 09 475 | 9/1992 |
| DE | 198 49 888 | 5/2000 |
| DE | 697 18 919 | 9/2003 |
| EP | 1 384 490 | 1/2004 |
| JP | 2001033461 | 2/2001 |
| WO | 01/43473 | 6/2001 |
| WO | WO02051471 A1 | 7/2002 |
| WO | 03/074110 | 9/2003 |

* cited by examiner

Primary Examiner—Brent Swarthout
(74) Attorney, Agent, or Firm—Dorsey & Whitney LLP

(57) ABSTRACT

A device including a display for displaying operational and/or functional parameters of the device and a control unit with at least one control element for controlling the display and/or device, wherein the display is at least partly rotatable with respect to the device, and/or wherein the position of the at least one control element is modifiable or changeable with respect to the device. In some embodiments, the control functions of at least two control elements of the device are interchangeable. In some embodiments, the display is provided by data sent to the display at intervals, whereby the display is updated. In embodiments in which several display parts are rotatable, data is processed by a processing module prior to being sent to the display. A method of display and/or display and control manipulation is encompassed.

21 Claims, 3 Drawing Sheets

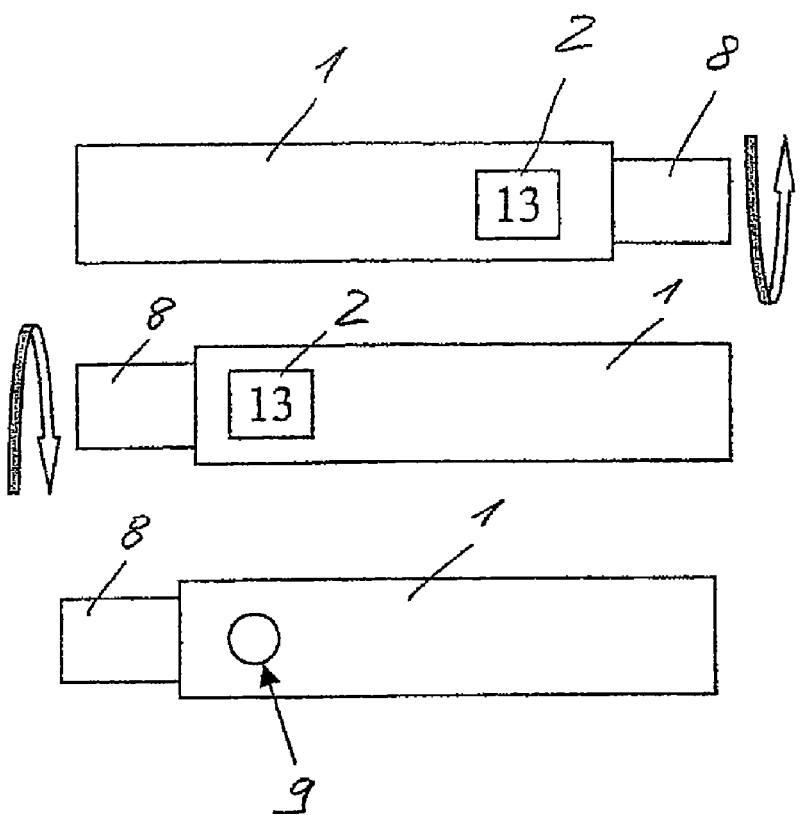

DEVICE WITH DISPLAY AND CONTROL

CROSS-REFERENCE TO RELATED APPLICATION(S)

This application is a continuation of International Application No. PCT/EP2005/002696, filed on Mar. 14, 2005, which claims priority to German Application No. 10 2004 013 415.4, filed on Mar. 18, 2004, the contents of both of which are incorporated in their entirety by reference herein.

BACKGROUND

The present invention relates to devices for administering, delivering, injecting, infusing or dispensing substances, and methods of making and using such devices. More particularly, it relates to a portable device for medical, pharmaceutical or cosmetic uses, e.g., for the administering and/or monitoring the administration of a medical product, wherein the device is provided with a display for displaying or indicating operational and functional parameters of the device.

In medical, pharmaceutical or cosmetic treatment methods, it is often necessary for a treatment device to be carried on the user's person. For treatment of diabetes, for example, the patient carries an insulin pump, so as to be able to check and meet his or her insulin requirements. To monitor the function of the pump, the insulin requirement, the insulin delivery and various other parameters, insulin pumps typically have a display for these operational and functional parameters. Insulin pumps also usually can be controlled by an associated or integrated control unit comprising several control elements that perform different functions. The control or modification of the pump setting, initiated by the control elements, is indicated on the display by way of corresponding operational and functional parameters.

Devices such as insulin pumps can be carried in different ways on the body, for example, fastened to a belt. The display and the control elements are arranged on the device in such a way that they allow the device to be read and operated when the device is being worn on the left-hand side of the body, so that it can be operated without difficulty by the right hand. However, if the device is worn on the right-hand side of the body, to operate it with the left hand the arrangement of the control elements is not suitable for simple, optimal operation and/or comfort. It is possible to turn the device through 180° so that the control elements are once again easy to reach. In this case, however, the display is difficult to read, since it is the wrong way around for the person wearing the device.

From other technical fields, data-processing units are known which, with the aid of a position sensor, measure the position of the data-processing unit with respect to a reference system, for example on the basis of gravity, and modify a display on a display field in accordance with the measured position. Such a data-processing unit is known from WO 014 3473, for example.

SUMMARY

It is an object of the present invention to make available a portable device for medical, pharmaceutical or cosmetic uses, which device can be easily operated and affords a high level of user comfort. In particular, in some embodiments, the device is to be able to be adapted so that it can be worn at different positions and in different orientations with respect to a user. It is a further object of the present invention to make available a method by which a display on a portable device can be easily read at different orientations of the device, i.e., by which the display on the device can be adapted to a specific orientation of the device.

In one embodiment, the present invention comprises a device comprising a display for displaying operational and/or functional parameters of the device and a control unit with at least one control element for controlling the display and/or device, wherein the display is at least partly moveable or rotatable with respect to the device, and/or wherein the position of the at least one control element is modifiable or changeable with respect to the device. In some embodiments, the control functions of at least two control elements of the device are interchangeable. In some embodiments, the display is provided by data sent to the display at intervals, whereby the display is updated. In embodiments in which several display parts are rotatable, data is processed by a processing module prior to being sent to the display.

In one embodiment, the present invention involves a device with a display and at least one control, and comprises a method of display manipulation, control manipulation, and/or display and control manipulation.

In one embodiment, the present invention comprises a device comprising a display for displaying at least operational and functional parameters of the device and a control unit comprising at least one control element, wherein the display is at least partially rotatable with respect to a housing of the device. In one embodiment, a position of the at least one control element with respect to the housing can be changed, and/or a function of the at least one control element can be changed.

In one embodiment, the present invention comprises a device for medical, pharmaceutical or cosmetic uses, which is portable and comprises a display for operational and/or functional parameters of the device and a control unit provided with at least one control element, in which the display is at least partially rotatable with respect to a housing of the device, and/or a position of the at least one control element with respect to the housing of the device can be changed, or a function of the at least one control element can be changed.

In one embodiment, the present invention comprises a method for rotating at least part of a display for operational and/or functional parameters of a device for medical, pharmaceutical or cosmetic uses, the display comprising a display field and a processing module, the method comprising the steps of generating a display on the display field by means of data for the display being sent at regular time intervals from a memory to the display field, the display thus being updated at the regular time intervals, and rotating at least one part of the display, the data from the memory being processed by the processing module in accordance with the rotating before being sent to the display field.

According to some embodiments of the present invention, a device for medical, pharmaceutical or cosmetic uses is designed to be portable. The device may be worn on a user's body so that it is not outwardly visible, or it can be placed in a pocket. However, it is also possible to carry the device about and to set it down in a fixed location, for example in proximity to the user. The present invention can also be applied to devices that are provided for controlling another fixed device for medical, pharmaceutical, cosmetic or other purposes, so as to be able to operate said further device remotely.

In some embodiments, a portable device in accordance with the present invention comprises a display for observing, viewing or monitoring operational and/or functional parameters of the device. From the display, the user is therefore able to read, for example, the operational settings of the device or treatment data and default settings. In some preferred embodiments, the display is formed by several display parts on a display field, such as an electronic display. The several display parts can indicate the various parameters of the device. For example, display parts may be provided for indicating the time, date, battery charge status, dose volume of a product to be administered from the device, or the number of product doses already delivered. In some embodiments, the display is preferably formed as an electronic illuminated display, for example as an LCD, LED or OLED array.

In some embodiments, the portable device further comprises a control unit with at least one, preferably several control elements for controlling the display and/or the device. In the case of several control elements, the different control elements each perform another function. For example, a control element can be provided which, for changing an operational or functional parameter, selects the corresponding parameter on the display. By means of two further control elements, for example in the form of a step-up button and a step-down button, it is then possible to correct the selected parameter upward or downward in quantity. For example, by actuating the step-up button, a product dose can be increased, and, by actuating the step-down button, a product dose can be reduced. The corresponding change in the product dose is displayed on the display by the display part for the dose volume.

According to some embodiments of the present invention, the display is at least partially rotatable with respect to a housing of the device, i.e., either the whole display or parts of the display are rotatable relative to the housing of the device. For this purpose, the display can be arranged on a display unit which is mechanically rotatable relative to the device housing. The display unit can, for example, be mounted rotatably or pivotably on the device housing and carry the display field. By rotating the display unit relative to the device housing, the display field with the display is likewise rotated with respect to the device housing.

In some preferred embodiments, the display with the several display parts is indicated on a display field which is fixed on the housing of the device. For this purpose, for example, a display is arranged directly on a side face of the housing. For rotation at least of one display part, this display part, for instance the quantity of the selected dose volume, is rotated on the display field. The different display parts of the display may also be displaceable on the display field.

In some embodiments, in addition to rotating the display or also, according to the present invention, instead of rotating the display, it is possible for the positions of at least two control elements to be modified or interchanged with respect to the device housing. For this purpose, it is possible for the control unit to be formed at least partially by a control means on which the control elements to be changed or interchanged are arranged and which is mechanically movable, e.g., rotatable, relative to the device housing. The control unit with the control elements can be mounted fixedly on the portable device, i.e., it is not detachable, but is nevertheless able to be rotated, pivoted or displaced relative to the device housing. By displacing or rotating the control unit, the position of the control elements arranged on the control means changes relative to the housing or the portable device. In doing so, in some embodiments, the control means is rotated relative to the device until a first control element has adopted the original position of a second control element and until the second control element has adopted the original position of the first control element, so that the positions of the control elements are interchanged. It is also possible, however, to bring the control means into any desired other setting, by which the position of the control elements is only changed.

It is also possible, in some embodiments of the present invention, to arrange the control elements fixedly relative to the portable device and to change only the function of a control element with the function of another control element. Interchanging the function of control elements can be done, for example, by a control element itself or by a menu item in a control menu for the device. Accordingly, for example, the buttons for a step-up or step-down function remain in principle at the same position or location on the device housing. However, after being interchanged, the original step-up button takes over the step-down function, and the original step-down button takes over the step-up function. It is of course also possible, in principle, for more than two control functions of control elements to be interchanged.

In some embodiments, the advantages of the present invention can be exploited either by simply rotating parts of the display or by changing or interchanging control elements relative to the device housing or interchanging the control functions of control elements. In some embodiments, it is advantageous, however, to use several possibilities of rotation, modification or interchanging, for example simultaneous rotation of the display and interchange of control functions.

In some preferred embodiments, in the control unit, one control element can be provided as a two-state or multi-state switch or continuous switch or a menu item in the control menu, by which the display is rotated through 180° relative to the device housing and/or the function of control elements is interchanged, in some preferred embodiments, at the same time. In this way, by a single press of a button, a device can be prepared to be worn in a position rotated through 180°. In some embodiments, by using a continuous switch, the display can be rotated steplessly with respect to its rotation angle orientation.

In some embodiments, a square electronic display is used. By such a square display, it is possible to retain the arrangement of display parts on the display field when the device or display is rotated through 90° or 180°.

In some embodiments, the rotating of the display and the changing or interchanging of control elements or control functions can take place manually, for example via a control element, in other embodiments, they can take place automatically. In a configuration for automatic rotation or interchanging, in one embodiment, the device comprises a sensor which measures the orientation of the device with respect to a reference system, e.g., with respect to the user. The rotation or interchanging of control elements then takes place in accordance with the sensor measurement, for example by a control signal emitted from the sensor. In some embodiments, the sensor can be a gravity sensor or a magnetic field sensor for the earth's gravity field or magnetic field.

With the aid of the invention, a portable medical, pharmaceutical or cosmetic device can be adapted to specific requirements of the user. It is thus possible, for example, for a left-handed person to take a device provided in principle for right-handed persons and to adapt it to individual requirements. It is therefore possible for a user to wear the device in what is a comfortable position, but without having to compromise on operating comfort.

In some embodiments, the present invention is provided, for example, for infusion pumps, e.g., insulin pumps. However, it is also advantageous, for example, for injection pens which are intended to be suitable for use both for left-handed and right-handed persons. Inhalers are further examples of administration devices for which the present invention is advantageous. The invention is also suitable, for example, for measurement devices for various physical parameters of a user, for example for measuring blood sugar levels.

In one embodiment, the present invention comprise a method for rotating at least parts of a display for displaying operational and/or functional parameters of a device for medical, pharmaceutical or cosmetic uses. The device comprises a display field on which the display is shown, and a processing module. In one embodiment of the method, a display is generated on the display field by dat, the data being sent at regular time intervals from a memory to the display field. The current data of a display are called up at regular intervals from the memory, and the display is updated according to this data. In this way, it is possible to ensure that the display is not disturbed by impacts or other influences which, for example, could render it incomplete or illegible. To be able to perform a rotation of at least parts of the display on the display field, the data are called up from the memory by the processing module and are processed in accordance with a desired rotation, before being sent to the display field. The processed data for a rotated display are stored in the memory, so that subsequently these data can be sent at regular intervals from the memory to the display field.

In some embodiments, the processing of the data for the display by the processing module can be triggered by a manual input, for example via a control element of the device, or by a menu item in the control menu of the device. It is also possible to provide the device with a sensor for measuring the orientation of the device with respect to a reference system, which sensor emits a signal to the processing module that triggers the processing of the data. In some embodiments, the processing module may comprise a microprocessor, computer or the like which calls up the data for the display from the memory and sends it to the display field. When the microprocessor receives a signal from an orientation measurement sensor or from a control element, the microprocessor calls up the data for the display from the memory, processes it according to a desired rotation, and then sends them to the display field.

In some embodiments, to generate the display on the display field, lines of the display field are successively filled from top left to bottom right according to the data from the memory. To generate a rotation of the display, the data from the memory are modified such that the lines of the display field are successively filled from bottom right to top left. In this way, a rotation through 180° is generated, for example. It is also possible to modify the data from the memory in such a way that the display field is no longer filled line by line, but instead column by column from top to bottom or from bottom to top. This results, for example, in a rotation through 90°. For this purpose, a square display field is advantageously used, for example a display with 96×96 pixels. The processing of the data from the memory for a desired rotation of the display is carried out in the microprocessor on the basis of a data-processing program which, for example, defines in which sequence the pixels of the display are to be filled. Two or more identical microprocessors may be provided in one device so that, if one microprocessor fails, it is possible to guarantee the display of the data essential to the user.

It is also possible, in principle, to use a conventional display module in which there is a program for rotation of a display according to the prior art. Such a module can, for example, be connected directly to a control element and the display.

BRIEF DESCRIPTION OF THE DRAWINGS

FIG. 4 shows another illustrative embodiment of a device in accordance with the present invention in a first orientation, FIG. 5 shows the device of FIG. 4 in an orientation in which it has been rotated through 180° relative to the first orientation, and FIG. 6 shows the device of FIG. 4 in a rear view.

DETAILED DESCRIPTION

Figure 1:
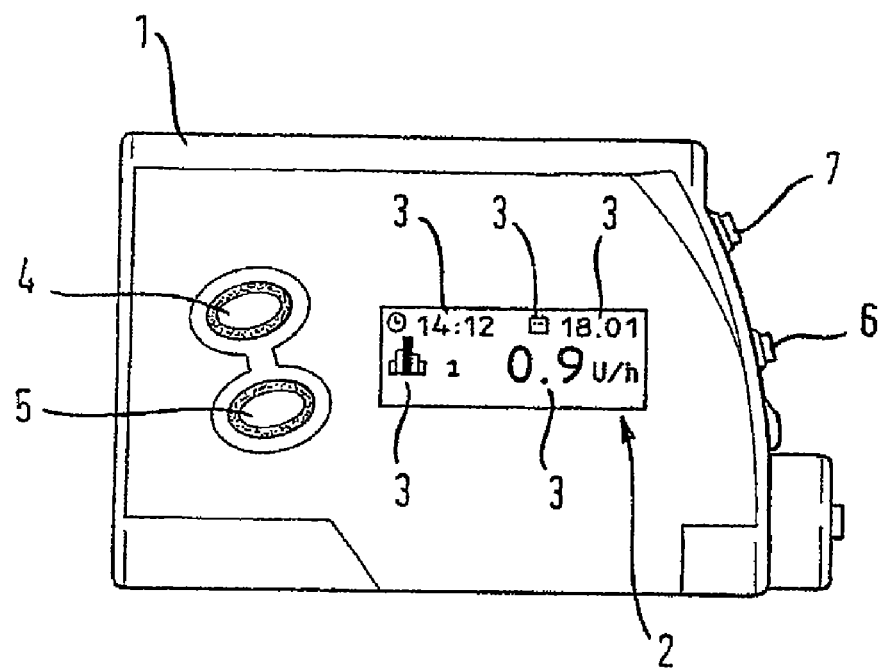
FIG. 1 shows an embodiment of a device in accordance with the present invention in a first illustrative embodiment and in a first orientation.

FIG. 1 shows a portable device in the form of an insulin pump which has a display field 2 on a side face of a housing of the device. The display field 2 contains a display with several display parts 3. In a first row on the display field 2, display parts 3 are provided for the time, battery operation and date. A second row contains a display part in the form of a bar chart for visual presentation of a selected volume of an insulin dose and the numerical quantity of the dose units delivered per hour. The insulin pump also has a control unit which comprises several control elements, in this illustrative embodiment four control elements 4, 5, 6 and 7. The control elements 4 and 5 are arranged next to the display field 2 on the side face of the housing 1 and are used, for example, for selecting the various display parts 3. The control elements 6 and 7 are arranged on a narrow side of the housing 1 of the insulin pump. The function of the control element 7 is one by which the display part selected by the control elements 4 and 5, or the operational or functional parameter indicated by this display part 3, is increased upward or in a forward direction, such that the control element 7 represents a step-up button. By contrast, the function of the control element 6 is one by which the parameter of the selected display part 3 is modified downward or backward. The control element 6 therefore forms a step-down button.

Figure 2:
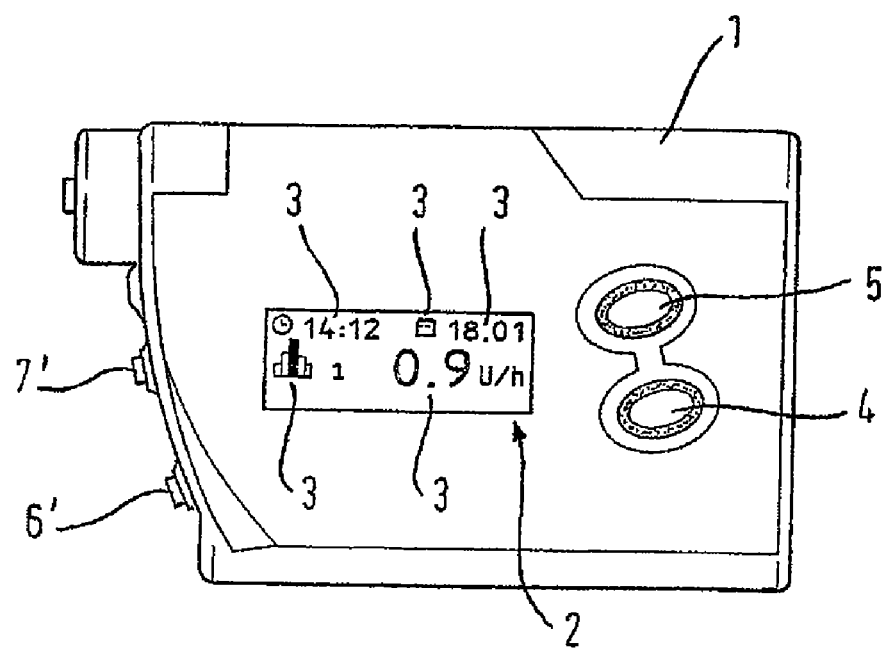
FIG. 2 shows the device of FIG. 1 in an orientation in which it has been rotated through 180° relative to the first orientation.

In FIG. 2, the insulin pump from FIG. 1 is shown in an orientation in which it has been turned through 180°. The display parts 3 of the display field 2 are likewise turned through 180° according to the rotation of the insulin pump. For changing the positions of the control elements 6 and 7, the step-up function of the control element 7 from FIG. 1 and the step-down function of the control element 6 from FIG. 1 have been interchanged. In this way, after the insulin pump has been rotated, the control element 7 from FIG. 1 serves, in FIG. 2, as control element 6' and provides the step-down function. Similarly, after rotation, the control element 6 from FIG. 1 provides the step-up function and thus forms, in FIG. 2, the control element 7'. According to the invention, the functions of the control elements 6 and 7 from FIG. 1 have been interchanged via a microprocessor (including any suitable hardware and/or software), for example, so that in FIG. 2 they each perform the respective other function. Therefore, the position of a control element for a defined function is also interchanged after rotation of the insulin pump. That is to say, in FIG. 1 the control element 7 arranged at the edge of the side face forms the step-up button and, in FIG. 2, the control element 7' arranged in the central area of the side face forms the step-up button.

Figure 3:
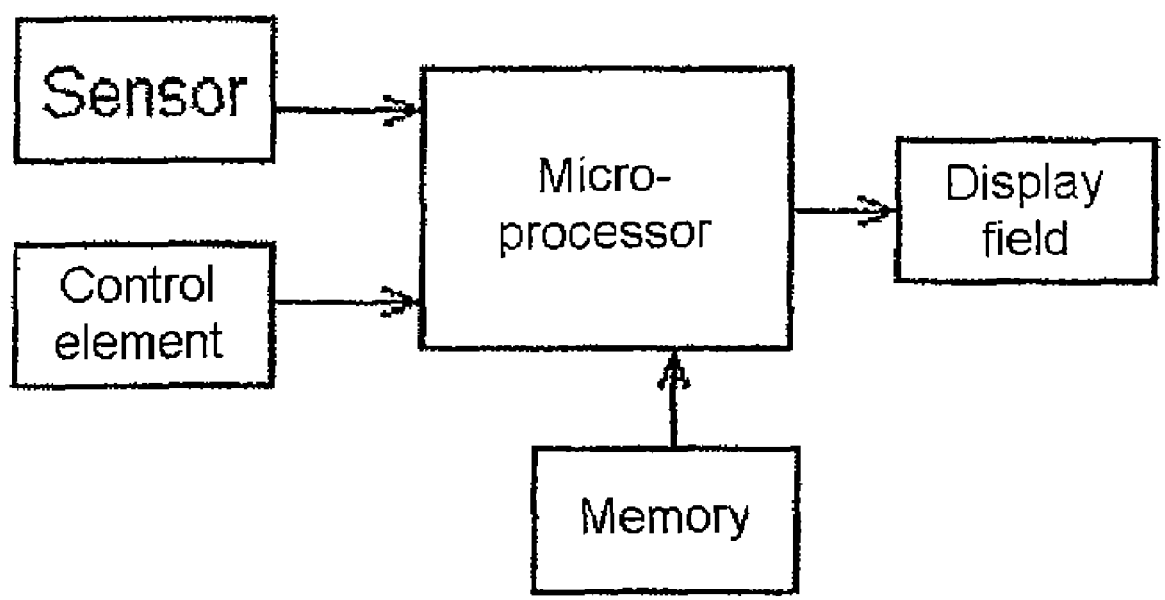
FIG. 3 shows a schematic representation of an embodiment of a method according to the present invention.

FIG. 3 shows a schematic representation of the method according to the invention. Accordingly, to generate the display on the display field, data for the display are called up at regular time intervals from a memory by a microprocessor, which serves as processing module (including any suitable hardware and/or software), and are sent to the display field. To execute a rotation at least of parts of the display, the microprocessor receives a signal from an orientation measurement sensor or from a control element. The microprocessor then processes the data called up from the memory in accordance with a desired rotation and sends the processed data for a rotated display to the display field, by which means the display appears in a rotated orientation.

FIG. 4 shows a portable device in the form of an injection pen, such as those that may be used for administering insulin or other substances. The injection pen has a slender housing 1 which, like the housing 1 of the pump, contains a reservoir with a product to be administered, and also a delivery means for delivering the product. A dosing button 8 protrudes from a proximal end of the housing 1. An optical display field 2 in the form of a flat screen is arranged in a proximal portion of the housing 1. The product dose selected by means of the dosing button 8 is displayed in the display field 2. As in the first illustrative embodiment, the display field 2 is segmented in the manner of known illuminated displays for showing numbers. The dose-selector button 8 can be rotated about a longitudinal axis of the device for selecting the product dose, and can be moved axially along the longitudinal axis for actuating the delivery means. FIG. 4 shows the device in a state in which the dose can be selected. In this dose-selector state, the dose-selector button 8 takes up a proximal end position relative to the housing. The dose-selector movement can be executed only in the proximal end position. When the dose-selector button 8 is moved in the distal direction up to a distal end position, the selected dose is dispensed.

In the state shown in FIG. 4, the device is set up for people who are right-handed. In the reading direction, the proximal (rear) end of the housing 1 is situated proximally (rearwardly) from the display field 2, the reading direction running from distal (front) to proximal (rear).

FIG. 5 shows the device of the second illustrative embodiment in a state for people who are left-handed. To operate the dose-selector button 8, the device is rotated, relative to the orientation shown in FIG. 4, through 180° about an axis that is transverse to the longitudinal axis. Accordingly, the display field 2 is also rotated. However, the light segments of the display field 2 are by software in accordance with the above-described method. The reading direction of the display field 2 is likewise rotated through 180° within the display field 2 and is in this sense "reversed", i.e., the reading direction now runs from proximal (rear) to distal (front). The dose-selector button 8 is now located proximally (rearwardly) from the display field 2 counter to the reading direction.

FIG. 6 shows a reverse face of the device of the second illustrative embodiment, directed away from the display field 2. A control element 9 can be seen which, when actuated, causes the display formed on the display field 2 to be rotated, to convert the device according to whether the respective user is right-handed or left-handed. The control element 9 is formed as a press switch. It is arranged in a recessed position in the housing 1, so that it cannot be activated accidentally. It is also so small that it cannot be pressed just by a finger, but instead only with a pin-like auxiliary means, for example with the tip of a ballpoint pen. The control element 9 can be a reset button with which the display can be set to "zero". However, the control element 9 can also be used exclusively for converting the device from right-handed to left-handed operation, the conversion being, in some embodiments, reversible.

In some embodiments, the device is preferably formed in such a way that the conversion from right-handed to left-handed operation, and preferably also the reverse conversion, can be carried out only when the dose-selector button 8 assumes the position, relative to the housing 1, in which the dose is selectable, i.e. when it assumes the proximal (rear) end position.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for delivering an injectable substance in doses, the device comprising:
    a housing configured to hold a reservoir disposed therein containing the product to be administered;
    a delivery means for delivering the product from the reservoir in doses;
    a display arranged on an exterior of the housing for displaying at least operational and functional parameters of the device, wherein the display is at least partially rotatable with respect to the housing of the device; and
    a control unit comprising one or more control elements, the control unit configured such that a position of one or more control elements can be changed with respect to the housing or a function of the control element can be changed;
    wherein at least one control element comprises a dose-selector button having a first position and a second position, wherein the rotation of the display or the change of position or a function of the at least one control element takes place in the first position of the dose-selector button.

2. The device as claimed in claim 1, wherein the control unit comprises a plurality of control elements each with a different function, and at least two of the control elements are interchangeable in respect of their function, the respective position of these at least two control elements on the housing being fixed.

3. The device as claimed in claim 1, wherein the display is arranged on a display unit which is mechanically rotatable relative to the housing of the device.

4. The device as claimed in claim 1, wherein the control unit is formed at least partially by a control means which is mechanically movable relative to the housing of the device.

5. The device as claimed in claim 1, wherein the display comprises a plurality of display parts on a display field, the display field being fixed on the housing of the device, at least one of the display parts being rotatable on the display field.

6. The device as claimed in claim 5, wherein the at least one of the display parts is displaceable on the display field.

7. The device as claimed in claim 1, wherein the control unit comprises at least two control elements and the arrangement of the control elements on the housing of the device is fixed, the control function of the at least two control elements is interchangeable.

8. The device as claimed in claim 5, wherein the display field is square.

9. The device as claimed in claim 5, wherein the display field is an electronic display field.

10. The device as claimed in claim 1, wherein the rotation at least of parts of the display, a changing or an interchanging of control elements and an interchanging of control functions takes place manually or automatically.

11. The device as claimed in claim 10, further comprising a sensor configured to measure the orientation of the device with respect to a reference system, and a rotation at least of parts of the display, a changing or an interchanging of control elements and an interchanging of control functions takes place in accordance with the sensor measurement.

12. The device as claimed in claim 11, wherein the control unit comprises a switch upon whose actuation the display is rotated, the position of the at least one control element is changed or the functions of control elements of the control unit are interchanged.

13. The device as claimed in claim 12, wherein the switch is arranged in a recessed position on the housing and is formed as a push-button.

14. The device as claimed in claim 12, wherein the switch is shaped and arranged on the housing in such a way that it can be actuated only by means of a thin actuating pin.

15. The device as claimed in claim 12, in which the switch is formed by a reset button upon whose actuation the display can be reset to a selected state.

16. A device for delivering an injectable substance, the device comprising:
   a housing configured to hold a reservoir containing the product to be administered;
   a delivery means for delivering the product from the reservoir;
   a display arranged on an exterior of the housing for displaying at least operational and functional parameters of the device; and
   a control unit comprising at least one control element, one of the control elements comprising a dose selection position and a dispensing position, wherein when the control element is arranged in the dose selection position, the display is at least partially rotatable with respect to the housing of the device, and when the control element is arranged in the dispensing position, the display is non-rotatable with respect to the housing of the device.

17. The device as claimed in claim 16, wherein the control unit comprises a switch upon whose actuation, and when the control element is arranged in the dose selection position, the display is at least partially rotated.

18. The device as claimed in claim 17, wherein the switch is arranged in a recessed position on the housing and is formed as a push-button.

19. The device as claimed in claim 17, wherein the switch is shaped and arranged on the housing in such a way that it can be actuated only by means of a thin actuating pin.

20. The device as claimed in claim 17, wherein the switch comprises a reset button upon whose actuation the display can be reset to a selected state.

21. The device of claim 1, wherein the first position of the dose-selector button corresponds to a dose selecting position and the second position corresponds to a dose dispensing position, wherein in the dose selecting position, the dose-selector button is for selecting a dose of the product to be administered by the device, and is configured to execute a dosing movement relative to the housing, and, in the dose dispensing position, the dose-selector button is for administering the selected dose, and is configured to execute a dispensing movement.

* * * * *